(12) United States Patent
Anderson

(10) Patent No.: US 6,353,003 B1
(45) Date of Patent: Mar. 5, 2002

(54) METHOD FOR REDUCING LEVELS OF HOMOCYSTEINE AND C-REACTIVE PROTEIN

(75) Inventor: Pamela Wang Anderson, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/303,618

(22) Filed: May 3, 1999

Related U.S. Application Data
(60) Provisional application No. 60/089,601, filed on Jun. 17, 1998.

(51) Int. Cl.$^7$ .............................................. A61K 31/445

(52) U.S. Cl. ....................... 514/324; 514/410; 514/422; 514/443; 514/448

(58) Field of Search ................................ 514/324, 410, 514/422, 443, 448

(56) References Cited

U.S. PATENT DOCUMENTS

| | | | |
|---|---|---|---|
| 4,133,814 A | 1/1979 | Jones et al. | |
| 4,380,635 A | 4/1983 | Peters | |
| 4,418,068 A | 11/1983 | Jones | |
| 5,075,321 A | 12/1991 | Schreiber | |
| 5,393,763 A | * 2/1995 | Black et al. | 514/333 |
| 5,441,947 A | 8/1995 | Dodge et al. | |
| 5,441,965 A | 8/1995 | Sall et al. | |
| 5,445,941 A | 8/1995 | Yang | |
| 5,464,845 A | 11/1995 | Black et al. | |
| 5,476,862 A | 12/1995 | Calnek et al. | |
| 5,482,949 A | 1/1996 | Black et al. | |
| 5,510,357 A | 4/1996 | Palkowitz | 514/324 |

FOREIGN PATENT DOCUMENTS

| | | |
|---|---|---|
| EP | 0659427 A1 | 12/1994 |
| EP | 0664121 A1 | 12/1994 |
| EP | 0664126 A1 | 12/1994 |
| EP | 0843999 A1 | 11/1999 |
| JP | WO93/10113 | 5/1993 |
| WO | WO93/10741 | 6/1993 |
| WO | WO98/47365 | 4/1997 |
| WO | WO99/08525 | 6/1997 |

OTHER PUBLICATIONS

Walsh BW, et al., The Effects of hormone replacement therapy and raloxifene on C–reactive protein and homocysteine in healthy postmenopausal women: a randomized, controlled trial. *Journal of Clinical Endocrinology & Metabolism.* 85(1):214–8, Jan. 2000.

Walsh, et al., "Effects of raloxifene on serum lipids and coagulation factors in healthy postmenopausal women" JAMA The Journal Of The American Medical Assoc., vol. 279, No. 18 (1998).

Mijatovic, et al., "Postmenopausal hormone replacement risk estimators for cornary artery disease and cardiovascular protection" Gynecological Endocrinology, vol. 13, pp. 130–144, 1999.

"Randomized, double–blind, placebocontrolled study of the effects of raloxifene and conjugated equine estrogen on plasma homocysteine levels in healthy postmenopausal women" Fertility and (Mijatovic et al.).

Rao, A.V., "Coronary heart disease risk factors in women: focus on gender differences. Journal of the Louisiana State Medical on Society" vol. 150(2) 67–72, 1998.

Fryer, et al. "Homocysteine, a risk factor for premature vascular disease and thrombosis, induces tissue factor activity in endothelial cells" Arterioclerosis and Thrombosis, vol. 13, No. 9, 1049–8834 (1993).

Harpel, et al, "Homocysteine and other sulfhydryl compounds enhance the binding of lipoprotein(A) to fibrin: A potential biochemical link between thrombosis, atherogenesis, and sulfhydryl compound metabolism" Proceedings of The National Academy Of Sciences of USA., vol. 89 (1992).

Haverkate, et al. "C–reactive protein and cardiovascular disease" Fibrinolysis and Proteolysis, vol. 11, No. Suppl. 10 (1996).

Chae, et al., "Postmenopausal hormone replacement therapy and cardiovascular disease" Thrombosis and Haemostasis vol. 78, No. 1 pp. 770–780 (1997).

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholecterol in the Absence of Uterine Stimulation in Ovariectomized Rats", Am Soc. Bone & Min. Res., Tampa, Sep. 18–22, 1993.

Bryant et al., "Raloxifene is a Tissue Specitfic Estrogen Agonist", Am Soc. Bone & Min. Res., Tampa, Sep. 18–22, 1993.

(List continued on next page.)

*Primary Examiner*—Dwayne C. Jones
*Assistant Examiner*—C. Delacroix-Muirheid
(74) *Attorney, Agent, or Firm*—Dan L. Wood; William R. Boudreaux; James J. Sales

(57) ABSTRACT

The current invention relates to a method for decreasing levels of homocysteine and/or C-reactive protein in humans comprising administering to a mammal in need thereof an effective amount of a compound of formula I:

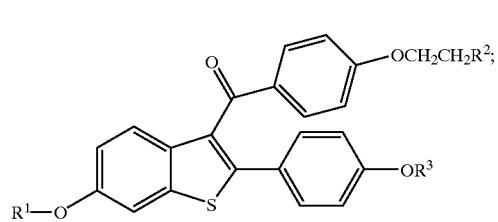

or a pharmaceutical salt or solvate thereof.

21 Claims, No Drawings

OTHER PUBLICATIONS

Frolick et al., "In Vivo and In Vitro Metabolism of Raloxifene", Am. Soc. Bone & Min. Res., Tampa, Sep. 18–22, 1993.

Glasebrook et al., "Multiple Binding Sites fro the Anti–estrogen Raloxifene", Am Soc. Bone & Min. Res., Tampa, Sep. 18–22, 1993.

Hock et al., "Combination of Raloxifene and Hume Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;".Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al."Uterine Bioassay of Tamoxifen, and New Estrogen Antagonist (LY117018) in Rats and Mice, " Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L.J. "Biological Actions and Binding Properites of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Cehmistry 22;1976, 962–966.

Black et al., Antiestrogens 2. Structure Activity Studies in a Series of 3–Aroyl–2–arylbenzo[b] thiophene Derivatives Leading to [6–Hydroxy–2–(4hydroxyphenyl)benzo[b] thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Evans, et al., "The effects of raloxifene on tibia histomorphometry in ovariectomized rats", Endocrinology, vol. 134, No. 5, pp. 2283–2288 (1994).

Hendrick, et al., "Tamoxifen and thromboembolism", JAMA, vol. 243, No. 6, pp. 514–515 (1980).

Database Dialog File 445, Dialog Accession No. 0004016, Products nearing market with Lilly (1993).

Database Dialog File 187, FDC Reports, Accession No. 00089403, vol. 55, No. 16, "Lilly's raloxifene entering phase III for osteoporosis" (1993).

Kangas, et al., "Agonistic and Antagonistic Effects of Antiestrogens in Different Target Organs", ACTA Oncologica, vol. 31, No. 2, pp. 143–146 (1992).

Cummings, et al., "the Effect of Raloxifen on Risk Of Breast Cancer in Postmenopausal Women" Results from the More Randomized Trial, JAMA, vol. 281, No. 23 (1999).

Delmas, et al., "Effects on Raloxifene on Bone Mineral Density, Serum Cholesterol Concentrations, and Uterine Endometrium in Postmenopausal Women", The New England Journal of Med., vol. 337, No. 23 (1997).

Anderson, et al., "Raloxifene Favorably Alters SErum Lipids in Postmenopausal Women with Cardiovascular Risk Factors" Circulation 98, 1–7, Abstract 34 (1998).

Paul, et al, "Effects of Raloxifene and Hormone Replacement Therapy of Homocysteine and C–Reactive Protein Levels in Postmenopausal Women" Circulation 98, 1–7, Abstract 35 (1998).

\* cited by examiner

METHOD FOR REDUCING LEVELS OF HOMOCYSTEINE AND C-REACTIVE PROTEIN

This Application claims the benefit of U.S. Provisional Application No. 60/089,601, filed Jun. 17, 1998.

FIELD OF THE INVENTION

The present invention deals with the disciplines of medicinal chemistry, cardiovascular physiology, and pharmacology. Specifically, the present invention is related to decreasing known risk factors of cardiovascular disease and other related symptoms associated with increased levels of homocysteine and C-reactive protein by administering certain 2-aryl-3-aroylbenzo[b]thiophenes.

BACKGROUND OF THE INVENTION

Cardiovascular disease is a major cause of death in the United States and a major source of morbidity, medical cost, and economic loss to millions of people. Two of the most common and destructive aspects of cardiovascular disease are the appearance of atherosclerosis and thrombolitic events.

In recent years, a great deal of progress has been achieved in the treatment of cardiovascular disease. This progress has been possible not only because of the advancement of therapeutic intervention in the disease mechanisms, but also through the early identification of patients at risk of developing the disease. Indeed, patient risk identification and early treatment are important features of modern medical practice. Over the last twenty years, a variety of factors and clinical parameters have been identified which correlate with either the current state or the future probability of developing cardiovascular disease. Such risk factors may include measurable biochemical or physiological parameters, e.g., serum cholesterol, HDL, LDL, fibrin levels, etc., or behavioral of life-style patterns, such as obesity, smoking, etc. (For further information see: "Cardiovascular risk factors in the elderly", Kannel W., *Coronary Artery Disease*, 8:565–575, 1997 and references cited therein.) Risk factors most germane to the present invention are levels of homocysteine and C-reactive protein.

The intrinsic relationship between a measurable parameter or risk factor and the disease state is not always clear. In other words, it is not always clear whether the risk factor itself is causative or contributory to the disease or is instead an ancillary reflection that is indicative of the disease. Thus, a therapeutic modality, which effects a risk factor, may be directly modifying a pathological mechanism of the disease and its future course, or may be indirectly benefiting some contributory process related to the disease.

Additionally, many risk factors associated with cardiovascular disease are involved in other pathological states in either a causative or indicative role. Therefore, improvement in a particular risk factor in cardiovascular disease may have other beneficial effects in other diseases related to that risk factor. For example, several conditions are known to be associated with abnormally high homocysteine levels, including genetic defect, menopause, hypercholesterolemia, smoking, hypertension, renal failure, and deficiencies in vitamins $B_6$, $B_{12}$, and folic acid.

Of particular interest to the methods of the present invention is the reduction of cardiovascular risk factors associated with abnormally high levels of homocysteine and C-reactive protein. It has been shown in a number of clinical studies that high levels of homocysteine in the blood are positively linked with cardiovascular disease. Furthermore, in patients suffering from genetic abnormalities which cause an increase in homocysteine (homocysteinuria), there is a great increase of early onset cardiovascular disease and other pathological conditions, inter alia, occular pathologies, skeletal and peridontal abnormalities, central nervous system irregularities, etc.

Homocysteine is also an intermediate found in the biochemical pathway related to the synthesis of the amino acids glutathione, methionine, and cysteine. Abnormally high levels of homocysteine is indicative of a metabolic disorder in the biochemical synthesis of these amino acids and is, thus, predictive of disease states associated with abnormally low levels of these amino acids. For example, glutathione has known bio-protective anti-oxidant properties such as the cyto-protection of monocytes and macrophages from oxidized low density lipoproteins (LDL). The oxidative action of oxidized LDL's on monocytes and macrophages is thought to be a pathological mechanism in atherosclerotic arterial damage.

C-reactive protein is produced by the liver in response to cytokine production. Cytokines are produced as part of an inflammatory response in the body. Thus, C-reactive protein levels are a marker of systemic inflammatory activity. Chronic inflammation is thought to be one of the underlying and sustaining pathologies in cardiovascular disease.

At menopause, with the loss of estrogen, women's prevalence of cardiovascular disease increases. Also, the risk factors of cardiovascular disease increase, especially lipid (cholesterol and triglyceride), homocysteine, and C-reactive protein levels. Today, the most common method of preventing cardiovascular disease in post-menopausal women is Hormone Replacement Therapy (HRT). However, many women do not comply with this therapy because of the unpleasant side-effects, such as bloating, resumption of mensus, breast tenderness, fear of uterine and breast cancer, etc. Additionally, while HRT does lower cholesterol and homocysteine levels, HRT raises C-reactive protein levels. A new therapeutic agent which lowers these risk factors would be beneficial.

SUMMARY OF THE INVENTION

The present invention provides methods for decreasing levels of homocysteine and C-reactive protein in humans comprising administering to a human in need thereof an effective amount of a compound of formula I:

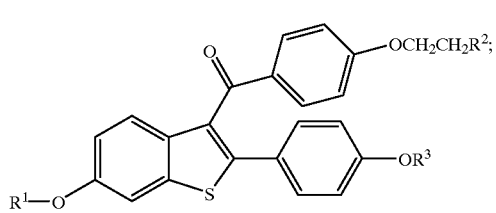

or a pharmaceutical salt or solvate thereof; wherein:
$R^1$ and $R^3$ are independently hydrogen, methyl, benzoyl, substituted benzoyl, or C(O)-($C_1$–$C_6$ alkyl);
$R^2$ is selected from the group pyrolidin-1-yl, piperidin-1-yl, and hexamethyleneimin-1-yl; where the $R^2$ group is optionally the N-oxide.

Further, the present invention relates to a method for inhibiting conditions or detrimental effects caused by an excess of homocysteine and/or C-reactive protein compris-

DETAILED DESCRIPTION OF THE INVENTION

The present invention is related to the discovery that a select group of 2-aryl-3-aroylbenzo[b]thiophenes, i.e., the compounds of formula I, are useful for lowering the levels of homocysteine and C-reactive protein.

As used herein, the term "effective amount" means an amount of a compound of formula I which is capable of decreasing levels of homocysteine and/or C-reactive protein and/or inhibiting conditions or detrimental effects caused by an excess of homocysteine and/or C-reactive protein.

The term "estrogen deficient" refers to a condition, either naturally occurring or clinically induced, where a woman can not produce sufficient estrogenic hormones to maintain estrogen dependent functions, e.g., menses, homeostasis of bone mass, neuronal function, cardiovascular condition, etc. Such estrogen deficient situations arise from, but are not limited to, menopause and surgical or chemical ovarectomy, including its functional equivalent, e.g., medication with GnRH agonists or antagonists, ICI 182780, and the like.

The term "inhibiting" in the context of inhibiting conditions or detrimental effects caused by an excess of homocysteine and/or C-reactive protein includes its generally accepted meaning, i.e., prohibiting, restraining, alleviating, ameliorating, slowing, stopping, or reversing the progression or severity of an increase of homocysteine and/or C-reactive protein and the pathological sequelae, i.e., symptoms, resulting from that event.

General terms used in the description of compounds herein described bear their usual meanings. For example, "$C_1$–$C_6$ alkyl" refers to straight, branched, or cyclic aliphatic chains of 1 to 6 carbon atoms including methyl, ethyl, propyl, iso-propyl, cyclopropyl, n-butyl, pentyl, hexyl and the like.

The term "substituted benzoyl" refers to benzoyl group having one to five substituents selected independently from the group: $C_1$–$C_4$ alkyl, $C_1$–$C_4$ alkoxy, hydroxy, nitro, chloro, fluoro, or tri(chloro or fluoro)methyl.

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977.

The term "solvate" represents an aggregate that comprises one or more molecules of the solute, such as a formula I compound, with one or more molecules of a pharmaceutical solvent, such as water, ethanol, and the like.

The methods provided by the present invention are useful in the treatment and prevention of pathologies associated with elevated levels of homocysteine (homocysteinuria). Harmful sequelae related to homocysteinuria, inhibited by the methods of the current invention, include, but are not limited to, ocular disorders (ectopia lentis, myopia, retinal detachment, g aucoma), skeletal disorders (scoliosis, dolic ostenomelia, osteoporosis) central nervous system defects, and the like.

The methods provided by the current invention are useful in both the treatment and prevention of harmful sequelae associated with elevated levels of C-reactive protein. Since C-reactive protein serum concentration is related to levels and production of cytokines which are especially produced in inflammatory processes, the methods of the current invention are useful in treating or preventing inflammatory events and sequelae, thereof. Such inflammatory events include, but are not limited to: arthritis (osteo and rheumatoid), arterial and venous chronic inflammation, auto-immune diseases, e.g., SLE, etc., and the like.

Methods of the current invention are useful for treating or preventing pathologic sequelae of atherosclerotic or thrombotic disease. Such pathologies include, but are not limited to stroke, circulatory insufficiency, ischemic events, myocardial infraction, pulmonary thromboembolism, stable and unstable angina, coronary artery disease, sudden death syndrome, and the like.

The present invention further contemplates the use of other currently known clinically relevant agents administered to treat the pathological conditions embodied in the present invention in combination with a compound of formula I.

Moreover, the present invention contemplates that the compounds of formula I are employed in either a treatment or prophylactic modality.

A preferred embodiment of the present invention is where the human to be administered a compound of formula I is female, and more preferred is when that human female is estrogen deficient.

Another preferred embodiment of the present invention is where the condition caused by an abnormally high level of homocysteine or C-reactive protein is cardiovascular disease, especially atherosclerosis and thrombosis. A particularly preferred embodiment of the present invention is the use of a compound of formula I in an estrogen deficient women, who is receiving estrogen or HRT, for the reduction of systemic or local inflammation.

Moreover, another preferred embodiment of the present invention is the use of a pharmaceutical acid addition salt of a compound of formula I where $R^1$ and $R^3$ are hydrogen and $R^2$ is pyrolidin-1-yl. More preferably, the salt is the hydrochloride. This more preferred compound is named [2-(4-hydroxyphenyl)-6-hydroxybenzo [b]thien-3-yl][4-[2-(1-pyrolidinyl)ethoxy]phenyl]methanone hydrochloride.

An even more preferred embodiment of the present invention is the use of a pharmaceutical acid addition salt of a compound of formula I where $R^1$ and $R^3$ are hydrogen and $R^2$ is piperidin-1-yl. Most preferably, the salt is the hydrochloride. This most preferred compound is named [2-(4-hydroxyphenyl)-6-hydroxybenzo [b]thien-3-yl][4-[2-(1-piperidinyl)ethoxy]phenyl]methanone hydrochloride or raloxifene hydrochloride.

Compounds of formula I where R and/or $R^3$ are hydrogen or methyl may be prepared according to known procedures, such as those detailed in U.S. Pat. Nos. 4,133,814, 4,418,068, and 5,731,342, the teachings of each are herein incorporated by reference. The compounds of formula I which are carboxylic esters ($R^1$ and/or $R^3$ are C(O)-($C_1$–$C_6$ alkyl), benzoyl, or substituted benzoyl) may be prepared from compounds of formula I where R and/or $R^3$ are hydrogen by methods described in U.S. Pat. No. 5,393,763, the teachings of which are herein included by reference.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

Pharmaceutical formulations can be prepared by procedures known in the art, such as, for example, in EP Published Application 670162A1, published Sep. 6, 1995, and in WO 97/35571 published Oct. 2, 1997, both of which are herein incorporated by reference. For example, a compound of formula I can be formulated with common excipients, diluents, or carriers, and formed into tablets, capsules, and the like.

Examples of excipients, diluents, and carriers that are suitable for formulation include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of formula I are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to decrease levels of homocysteine and/or C-reactive protein according to this invention will depend upon the particular circumstances of the conditions to be treated. Considerations such as dosage, route of administration, and frequency of dosing are best decided by the attending physician. Generally, an effective minimum dose for oral or parenteral administration of a compound of formula I is about 1, 5, 10, 15, or 20 mg. Typically, an effective maximum dose is about 800, 120, 60, 50, or 40 mg. A particularly effective amount is 60 mg of raloxifene hydrochloride (56 mg of free base) per day via an oral route of administration. Such dosages will be administered to a patient in need of treatment from one to three times each day or as often as needed to effectively decrease levels of homocysteine and/or C-reactive protein and/or inhibit conditions or detrimental effects caused by an excess of homocysteine and/or C-reactive protein.

The formulations which follow are given for purposes of illustration and are not intended to be limiting in any way. The total active ingredient in such formulations comprises from 0.1% to 99.9% by weight of the formulation. The term, "active ingredient" means a compound of formula I, or a pharmaceutical salt or solvate thereof, (preferably raloxifene hydrochloride). An even more preferred formulation of a compound of formula I would be raloxifene hydrochloride in the particular crystalline form, particle size, and composition illustrated in U.S. Pat. No. 5,731,327 and PCT application WO 97/35571 (Oct. 2, 1997) the teachings of each are incorporated by reference.

Formulation 1
Gelatin Capsules

| Ingredient | Quantity (mg/capsule) |
| --- | --- |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

Formulation 2
Tablets

| Ingredient | Quantity (mg/tablet) |
| --- | --- |
| Active Ingredient | 50–600 |
| Starch | 10–50 |
| Cellulose, microcrystalline | 10–20 |
| Polyvinylpyrrolidone (as 10% solution in water) | 5 |
| Sodium carboxymethyl cellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

Formulation 3
Aerosol

| Ingredient | Weight % |
| --- | --- |
| Active Ingredient | 0.50 |
| Ethanol | 29.50 |
| Propellant 22 (Chlorodifluoromethane) | 70.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4 Suspension | |
|---|---|
| Ingredient | Weight/ Volume |
| Active Ingredient | 100 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | 5 mL |

Suspensions each containing 100 mg of a compound of formula I per 5 mL dose are prepared as follows: the active ingredient is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the entire mixture to the required volume.

The following demonstration of the methods of the present invention is presented for the purposes of illustration and is not intended to limit the scope of this invention in any way.

A clinical investigation was conducted which included 390 women (45–72 years old), who were an average of ten years postmenopausal. These patients were randomly assigned to the following treatment protocol: raloxifene hydrochloride at 60 mg per day via oral administration (cf. Formulation 2, supra), raloxifene at 120 mg per day, or HRT therapy. Homocysteine and C-reactive protein baseline levels were determined, prior to the initiation of therapy. Methods for such determinations are well known and can be found in the references cited, supra. The study was conducted for a period of six months. The levels of homocysteine and C-reactive protein in each patient were compared at the end of six months with that patient's baseline. Results were analyzed by variance. Raloxifene at 60 mg per day lowered levels of homocysteine by 8% (p<0.05) and C-reactive protein by 4% (NS). Raloxifene at 120 mg per day lowered homocysteine by 5.7% (p<0.05) and C-reactive protien by −3.9 (NS). HRT lowered homocysteine by 6.6% (p<0.05), but raised C-reactive protein by 84.1% (p<0.05).

I claim:

1. A method for decreasing the level of homocysteine in humans comprising administering to a human in need thereof an effective amount of a compound of formula I:

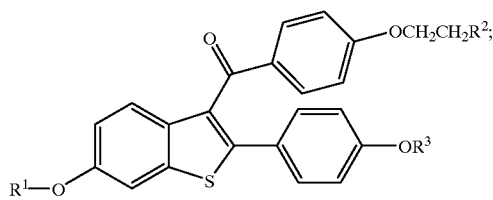

or a pharmaceutical salt or solvate thereof, wherein:
$R^1$ and $R^3$ are independently hydrogen, methyl, benzoyl, substituted benzoyl, or $C(O)$-$(C_1$-$C_6$ alkyl);
$R^2$ is selected from the group pyrolidin-1-yl, piperidin-1-yl, and hexamethyleneimin-1-yl; where the $R^2$ group is optionally the N-oxide.

2. A method for decreasing the level of C-reactive protein in humans comprising administering to a human in need thereof an effective amount of a compound of formula I:

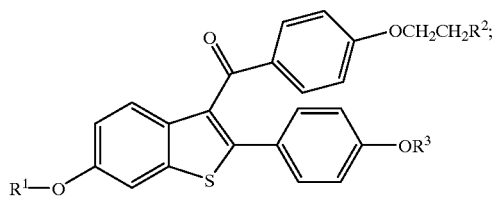

or a pharmaceutical salt or solvate thereof wherein:
$R^1$ and $R^3$ are independently hydrogen, methyl, benzoyl, substituted benzoyl, or $C(O)$-$(C_1$-$C_6$ alkyl);
$R^2$ is selected from the group pyrolidin-1-yl, piperidin-1-yl, and hexamethyleneimin-1-yl; where the $R^2$ group is optionally the N-oxide.

3. A method for inhibiting conditions or detrimental effects caused by an excess of homocysteine and/or C-reactive protein comprising administering to a human in need thereof an effective amount of a compound of formula I:

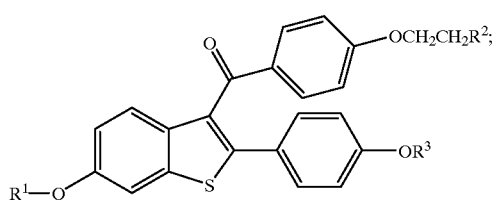

or a pharmaceutical salt or solvate thereof; wherein:
$R^1$ and $R^3$ are independently hydrogen, methyl, benzoyl, substituted benzoyl, or $C(O)$-$(C_1$-$C_6$ alkyl);
$R^2$ is selected from the group pyrolidin-1-yl, piperidin-1-yl, and hexamethyleneimin-1-yl; where the $R^2$ group is optionally the N-oxide.

4. The method according to claim 1 where the human is a female.

5. The method according to claim 4 where the female is estrogen deficient.

6. The method according to claim 5 where the compound of formula I is a pharmaceutical acid addition salt, $R^1$ and $R^3$ are hydrogen, and $R^2$ is piperidin-1-yl.

7. The method according to claim 6 where the compound of formula I is the hydrochloride salt.

8. The method according to claim 5 where the compound of formula I is a pharmaceutical acid addition salt, $R^1$ and $R^3$ are hydrogen, and $R^2$ is pyrolidin-1-yl.

9. The method according to claim 8 where the compound of formula I is the hydrochloride salt.

10. The method according to claim 2 where the human is a female.

11. The method according to claim 10 where the female is estrogen deficient.

12. The method according to claim 11 where the compound of formula I is a pharmaceutical acid addition salt, $R^1$ and $R^3$ are hydrogen, and $R^2$ is piperidin-1-yl.

13. The method according to claim 12 where the compound of formula I is the hydrochloride salt.

14. The method according to claim 11 where the compound of formula I is a pharmaceutical acid addition salt, $R^1$ and $R^3$ are hydrogen, and $R^2$ is pyrolidin-1-yl.

15. The method according to claim 14 where the compound of formula I is the hydrochloride salt.

16. The method according to claim 3 where the human is a female.

17. The method according to claim 16 where the female is estrogen deficient.

18. The method according to claim 17 where the compound of formula I is a pharmaceutical acid addition salt, $R^1$ and $R^3$ are hydrogen, and $R^2$ is piperidin-1-yl.

19. The method according to claim 18 where the compound of formula I is the hydrochloride salt.

20. The method according to claim 19 where the compound of formula I is a pharmaceutical acid addition salt, $R^1$ and $R^3$ are hydrogen, and $R^2$ is pyrolidin-1-yl.

21. The method according to claim 20 where the compound of formula I is the hydrochloride salt.

\* \* \* \* \*